United States Patent [19]
Montgomery

[11] Patent Number: 5,944,528
[45] Date of Patent: Aug. 31, 1999

[54] CHLORINE DIOXIDE TOOTH WHITENING COMPOSITIONS

[75] Inventor: R. Eric Montgomery, Monterey, Mass.

[73] Assignee: IDEX Dental Sciences, Inc., Monterey, Mass.

[21] Appl. No.: 08/901,261

[22] Filed: Jul. 28, 1997

Related U.S. Application Data

[60] Provisional application No. 60/022,384, Jul. 29, 1996.

[51] Int. Cl.$^6$ .............................. A61C 5/00; A61K 7/20; C01B 15/00; A61G 17/02
[52] U.S. Cl. .............................................. 433/215; 424/53
[58] Field of Search ........................ 424/49–58; 433/215

[56] References Cited

U.S. PATENT DOCUMENTS

| | | | |
|---|---|---|---|
| 1,435,498 | 11/1922 | Resnik | 424/53 |
| 4,330,531 | 5/1982 | Alliger | 424/53 |
| 4,689,215 | 8/1987 | Ratcliff | 424/53 |
| 4,891,216 | 1/1990 | Kross et al. | 424/661 |
| 4,902,498 | 2/1990 | Agricola et al. | 424/52 |
| 5,098,303 | 3/1992 | Fischer | 433/215 |
| 5,100,652 | 3/1992 | Kross et al. | 424/53 |
| 5,234,342 | 8/1993 | Fischer | 433/215 |
| 5,264,205 | 11/1993 | Kelly | 424/53 |
| 5,281,412 | 1/1994 | Lukacovic et al. | 424/53 |
| 5,376,006 | 12/1994 | Fischer | 424/53 |
| 5,409,631 | 4/1995 | Fischer | 424/53 |
| 5,573,399 | 11/1996 | McLintock | 433/215 |
| 5,622,725 | 4/1997 | Kross | 424/665 |
| 5,631,000 | 5/1997 | Pellico | 424/53 |
| 5,702,251 | 12/1997 | McLintock | 433/215 |
| 5,718,886 | 2/1998 | Pellico | 424/53 |
| 5,725,843 | 3/1998 | Fischer | 433/215 |
| 5,746,598 | 5/1998 | Fischer | 424/53 |
| 5,759,038 | 6/1998 | Fischer | 433/215 |
| 5,770,105 | 6/1998 | Fischer | 424/53 |
| 5,772,986 | 6/1998 | Kross | 424/53 |
| 5,785,527 | 7/1998 | Jensen | 433/215 |
| 5,816,802 | 10/1998 | Montgomery | 433/80 |

FOREIGN PATENT DOCUMENTS

| | | |
|---|---|---|
| 360299 A2 | 3/1990 | European Pat. Off. |
| 164472 B1 | 3/1992 | European Pat. Off. |
| 511782 A1 | 11/1992 | European Pat. Off. |
| 287074 B1 | 11/1993 | European Pat. Off. |
| 344701 B1 | 12/1994 | European Pat. Off. |
| 565134 B1 | 3/1996 | European Pat. Off. |
| 1469398 | 4/1977 | United Kingdom. |
| 2 289 841 | 6/1995 | United Kingdom. |
| 2 290 233 | 12/1995 | United Kingdom. |
| 2290233 | 12/1995 | United Kingdom. |
| 96/25916 | 8/1996 | WIPO. |
| 98/04235 | 2/1998 | WIPO. |

OTHER PUBLICATIONS

Loel, D. A., Use of acid cleanser in endodontic therapy, *Journal–American Dental Association*, vol. 90, pp. 148–151, Jan. 1975.

*Primary Examiner*—Shep K Rose
*Attorney, Agent, or Firm*—Bromberg & Sunstein LLP

[57] ABSTRACT

A composition having an effective dosage of chlorine dioxide for causing a visible change in the whiteness of a tooth surface is disclosed. The composition includes a first formulation having a chlorine dioxide precursor and a second formulation having an acidulant capable of generating chlorine dioxide upon contact with the precursor. Upon admixture of the first and second formulations to produce chlorine dioxide, the composition has a pH in the range of from about 3.0 to about 4.5. To whiten teeth, the first and second formulations may be mixed with one another prior to application of the resulting mixture to the teeth. Alternatively, one of the first and second formulations may initially be applied to the teeth prior to the application of the remaining formulation. The inventive composition is formulated to cause a visible change in the whiteness of a tooth surface in a relatively short period of time.

18 Claims, No Drawings

CHLORINE DIOXIDE TOOTH WHITENING COMPOSITIONS

RELATED U.S. APPLICATION

The present application claims priority from provisional application Ser. No. 0/022,384, filed Jul. 29, 1996, which is hereby incorporated herein by reference.

TECHNICAL FIELD

The present invention relates to improved dental compositions and methods for whitening teeth.

BACKGROUND ART

White teeth have long been considered cosmetically desirable. Unfortunately, teeth become almost invariably discolored in the absence of external intervention. The tooth materials which are generally responsible for presenting a stained appearance are enamel, dentin, and the acquired pellicle. In particular, tooth enamel is formed predominantly from inorganic material, mostly in the form of hydroxyapatite crystals, and further contains approximately 5% organic material, primarily in the form of collagen. Conversely, dentin is composed of about 20% protein, including collagen, with the balance comprising of inorganic material, predominantly hydroxyapatite crystals, similar to that found in enamel. The acquired pellicle, on the other hand, is a proteinaceous layer on the surface of tooth enamel which reforms rapidly even following an intensive tooth cleaning with highly abrasive prophylaxis pastes.

Tooth discoloration results from both extrinsic and intrinsic staining. Extrinsic staining of the tooth surface arises as a result of the accumulation of various chromogenic substances (in addition to chromogen precursors, which are initially colorless, but later chemically convert to chromogens) within the acquired pellicle. This type of staining can usually be removed by mechanical methods, which remove the acquired pellicle or portions thereof, along with the adherent chromogens. Aging of extrinsic stains, however, has been known to make the extrinsic stains less susceptible to removal by mechanical means, perhaps due to increased depth of extrinsic stain penetration into enamel over time. Such stains, therefore, require the use of chemicals, such as oxygenating agents, which can penetrate the tooth enamel to oxidize or solubilize the deep-seated chromogens. In contrast, intrinsic staining occurs as a result of chromogenic substances derived from sources within the tooth. This type of staining is not amenable to mechanical methods of tooth cleaning, and the aforementioned chemical methods are usually required.

Tooth-whitening compositions generally fall into two categories: (1) liquids, gels, or pastes, including toothpastes, that may be mechanically agitated at the stained tooth surface in order to effect tooth stain removal through abrasive erosion of stained acquired pellicle; and (2) liquids, gels, or pastes that accomplish the tooth-whitening effect by a chemical process while being in contact with the stained tooth surface for a specific period, after which the formulation is removed. In some cases the mechanical process is supplemented by an auxiliary chemical process, which may be oxidative or enzymatic.

The majority of professionally-monitored at-home tooth-whitening compositions act by oxidation. These compositions are dispensed into a custom-made tooth-whitening tray for use directly by a patient. Typically, these trays must be held in the mouth of the patient for a period of time often greater than about 60 minutes, and sometimes as long as 8 to 12 hours in order to produce any results. The slow rate of whitening is in large part the consequence of formulations that are developed to maintain stability of the oxidizing composition prior to use. These oxidizing compositions may contain a hydrogen peroxide precursor, for instance, carbamide peroxide, which is mixed with an anhydrous or low-water content, hygroscopic viscous carrier containing glycerin and/or propylene glycol and/or polyethylene glycol. When contacted by the moisture in saliva, carbamide peroxide dissociates into urea and hydrogen peroxide. Moreover, because of the slow rate of whitening with the hygroscopic carrier, the currently available tooth-whitening compositions containing carbamide peroxide can cause tooth sensitization in many patients. Tooth sensitivity is believed to result from the movement of fluid through the dentinal tubes toward nerve endings in the tooth. This fluid movement is enhanced by the carriers for the carbamide peroxide. In fact, it has been determined that glycerine, propylene glycol and polyethylene glycol can each give rise to varying amounts of tooth sensitivity following exposure of the teeth to heat, cold, overly sweet substances, and other causative agents.

Prolonged exposure of teeth to whitening compositions, as presently practiced in the industry, has a number of other adverse effects in addition to tooth sensitivity. These include: (i) solubilization of calcium from the enamel layer at pH less than 5.5 with associated demineralization, (ii) penetration of the intact enamel and dentin by the whitening agents, so as to reach the pulp chamber of a vital tooth thereby risking damage to pulpal tissue, and (iii) dilution of the whitening compositions with saliva with resulting leaching from the dental tray and subsequent digestion.

Furthermore, in situ decomposition of hydrogen peroxide in peroxide-based tooth whitening compositions can lead to the formation of free radicals such as hydroxyl and per hydroxyl radical species, which are highly reactive molecules that have been implicated in the formation of cancerous cells. Although the use of hydrogen peroxide at concentrations of up to 3% by weight in oral care products has recently been deemed safe for everyday use in the United States, many regulatory agencies throughout the world have placed an upper limit on the amount of hydrogen peroxide permitted for such applications. For instance, the European Community Cosmetic Directive, which regulates the permissible level of additives in various products, has established the upper limit for hydrogen peroxide at 0.1% by weight of an oral care composition. This level is insufficient for effecting a tooth whitening effect in a reasonable period of time.

As there is a cosmetic need for whitening teeth while avoiding the adverse effects usually associated with prolonged exposure to tooth whitener having peroxide, it is desirable to provide a non-peroxide tooth whitening composition capable of whitening the teeth in a reasonably short period of time.

SUMMARY OF THE INVENTION

The present invention relates to the use of chlorine dioxide ($ClO_2$) to satisfy the need for a non-peroxide tooth whitening composition that can of quickly and safely oxidize tooth staining chromogens to whiten teeth.

Chlorine dioxide is a greenish yellow gas which is soluble in water and is a strong oxidizer. In low volume applications, such as water treatment and disinfection, chlorine dioxide is usually produced by the acidification of an aqueous solution of sodium chlorite ($NaClO_2$). Chlorine dioxide reacts with organics as an oxidant with little or no chlorination, thereby making it safer to use in water treatment applications than chlorine gas ($Cl_2$). The aqueous solution of chlorine dioxide resulting from this conversion is greenish yellow in color and has a maximum absorption of around 360 nanometers (nm). In general, an aqueous solution of chlorine dioxide is relatively unstable to heat and light, and is manufactured in situ from alkali metal chlorite or chlorate salts at the point of use. Chlorine dioxide is particularly effective as an oxidant of phenolic compounds, and also has particular utility in the paper and pulp industries. In addition, chlorine dioxide has been used as an antimicrobial ingredient in oral care preparations. However, it is believed that chlorine dioxide has not been used as a tooth whitening agent.

In accordance with an embodiment of the present invention, relatively low concentrations of chlorine dioxide, preferably in the range of 1 to 500 parts per million (based on total weight of the composition), when contained in or released by tooth whitening compositions, are effective and useful in whitening teeth. The chlorine dioxide contained in or released by tooth whitening compositions, when placed in contact with the tooth surface, is observed to rapidly oxidize tooth stains, rendering the treated tooth surface relatively whiter after the contact.

Since chlorine dioxide may not be stable for extended periods of time, it is necessary to prepare, package and store the tooth whitening compositions of the present invention in two separate formulated portions. In an embodiment of the invention, one portion contains a chlorine dioxide precursor (CDP), such as sodium chlorite, and another portion contains an acidulant (ACD). The CDP portion is generally formulated to have a pH in excess of 7.0 in order to prevent premature generation of chlorine dioxide during storage. The ACD portion, on the other hand, is generally formulated so that when it combines with or contacts the chlorine dioxide precursor, chlorine dioxide is released from the precursor and the resulting composition or interface has a pH of less than 7.0. An example of the inventive tooth whitening composition includes a gelled aqueous CDP portion containing 5000 parts per million of sodium chlorite, and a gelled ACD portion containing 2.0% anhydrous citric acid. The composition formed from an admixture of the two portions may be placed in contact with a stained tooth surface to effect whitening.

To whiten teeth, in accordance with one embodiment of a method of the present invention, the two formulated portions may be mixed thoroughly prior to placing the entire admixed composition into a custom fabricated ethylene vinyl acetate dental tray. Such a tray is disclosed in U.S. application Ser. No. 08/533,148, entitled "Dental Tray", filed Sep. 25, 1995, now U.S. Pat. No. 5,816,802, issued on Oct. 6, 1998 in the name of the present inventor, and is hereby incorporated herein by reference. The dental tray with the inventive composition is then placed in the mouth for a predetermined period of time. During this period, the tooth surface is whitened through the oxidative action of chlorine dioxide on chromaphores entrapped within the acquired pellicle, enamel, and dentin structures of the tooth. After the predetermined period, the tray is taken out, and excess mixed gel compositions removed from the tooth surfaces. Alternatively, the two portions may be mixed and brushed directly onto the stained tooth or teeth.

In accordance with another embodiment of the method of the present invention, an interface is provided between the CDP portion and the ACD portion in order to generate chlorine dioxide at the interface to effect tooth whitening. For example, a stained tooth surface may initially be placed in contact with one of the CDP and ACD portions, and subsequently placed in contact with the remaining portion so that an interface may be formed at the boundary where both portions remain in contact with or adjacent to the stained tooth surface. The tooth surface is thereafter whitened through the oxidative action of chlorine dioxide generated within the interface. The sequential application of each of the CDP and ACD portions may be accomplished by the use of a dental tray or by brushing, if for example, the portions are in the form of a dentifrice (i.e., paste or powder) or gel. If application of the second formulation is accomplished using a dental tray, the tray may be removed after a tooth has been exposed to chlorine dioxide generated proximate to the tooth for a time period of between approximately five minutes and approximately sixty minutes. If, on the other hand, both or at least one of the CDP and ACD portions is a liquid (i.e., mouth rinse), the sequential application can be accomplished, at least in part, by rinsing.

DETAILED DESCRIPTION OF THE INVENTION

As it is necessary to manufacture, package and store the invention composition in two separate portions, the components and characteristics of each portion will first be described individually. A description of the characteristics and modes of application for the combined portions then follows.

The chlorine dioxide precursor (CDP) portion of the inventive compositions contains a stable compound capable of producing or releasing chlorine dioxide upon contact or admixture with the acidulant (ACD) portion. In a preferred embodiment, chlorine dioxide precursors are selected from the group consisting of alkali metal chlorites and alkali metal chlorates. An example of an alkali metal chlorate is sodium chlorite. Sodium chlorate is available commercially as an 80% purity material with varying amount of other salts, such as sodium chloride, included therein for stability and ease of handling. The American Water Works Association has established specifications for sodium chlorite to be used in treating potable water. In particular, technical grade solid sodium chlorite should not contain less than 78.0% $NaClO_2$. Furthermore, the impurity limits for 80% assay sodium chlorite should not be more than 17.0% sodium chloride, 3.0% sodium carbonate, 3.0% sodium sulfate, and 0.0003% arsenic. Solution grades of sodium chlorite are also available and, similarly, have varying amounts of auxiliary salts and buffers for stabilization.

Depending upon the mode of application, the CDP portion may contain a variety of auxiliary components for the purpose of stabilizing, thickening, or otherwise improving its performance in whitening teeth. Such components must be carefully screened for compatibility with the chlorine dioxide precursors. Flavorants and sweeteners are generally not required in the CDP portion. However, carefully screened flavorants and sweeteners may find utility in the inventive composition. In addition, preservatives are generally not required, due to the antimicrobial properties of the chlorine dioxide precursors.

Stabilizers for the CDP portion include, but are not limited to, alkali metal chlorides and alkali metal carbonates. Thickeners include, but are not limited to, hydroxyethylcellulose, polyethylene glycol and polyoxyethylene. Performance enhancers include, but are not limited to, non-ionic surfactants such as poly(ethylene oxide-co-propylene oxide) block copolymers.

The ACD portion contains, on a fundamental level, an aqueous carrier and a water-soluble acidulant. Suitable water-soluble acidulants include citric acid, malic acid, fumaric acid, and other non-toxic, orally acceptable acidulants. The water-soluble acidulant may also be a polymeric compound, such as carboxypolymethylene, which can simultaneously serve as a viscosity modifier. Polymeric acidulants with molecular weights in excess of 100,000 are preferred over their lower molecular weight counterparts, due to the reduced solubilization of enamel calcium observed with higher molecular weight entities.

The ACD portion may also include auxiliary components including thickeners, performance enhancers, and preservatives. Suitable thickeners include partially neutralized carboxypolymethylene, polyoxyethylene, xanthan gum, and other acid-stable polymers. It is preferred that all auxiliary components contained in the ACD portion be relatively resistant to oxidation by chlorine dioxide, since oxidation of composition components by chlorine dioxide after admixture or contact of the CDP and ACD portions will reduce the availability of chlorine dioxide. To this end, the chances of oxidation and/or solubilization of tooth stain chromogens by chlorine dioxide are also reduced.

The CDP portion is preferably formulated at pH in excess of about 7.0, and most preferably at a pH in the range of from about 7.5 to about 9.0. The ACD portion is preferably formulated at a pH of less than about 6.0, and most preferably at a pH in the range of from about 3.0 to about 4.5. The pH of the mixed portions (either admixed homogeneously or at the contact interface between the two portions) is preferably less than about 6.0 and most preferably in the range of from about 3.0 to about 4.5.

An example of the inventive composition is presented below:

EXAMPLE 1

CDP Portion

| Ingredient | Amount |
| --- | --- |
| Deionized water | 983.3 grams |
| Sodium chlorite, technical grade | 16.7 grams |
| Total | 1000.0 grams |

The CDP portion above was manufactured by adding the sodium chlorite to the deionized water in a HDPE container with constant stirring until a clear solution was obtained. The resulting liquid solution, which was transparent and had a pH of about 8.2, was packaged and stored in light-resistant ½ ounce HDPE bottles with dauber-type pressure-actuated closures.

ACD Portion

| Ingredient | Amount |
| --- | --- |
| Deionized water | 913.1 grams |
| Glycerin 99.7% USP | 50.0 grams |
| Methylparaben NF | 1.5 grams |
| Carbopol 974P-NF | 50.0 grams |
| Citric acid anhydrous USP | 3.0 grams |
| Sodium hydroxide USP | 2.4 grams |
| Total | 1000.0 grams |

The ACD portion was manufactured by weighing out the deionized water (less 30.0 grams to dissolve the sodium hydroxide in the final neutralization step) in a plastic or glass container, then adding the methylparaben, glycerin, and citric acid anhydrous sequentially while stirring constantly. When a clear solution was obtained, the Carbopol 974P-NF was slowly sifted into the vortex of the stirred liquid until a milky dispersion was obtained. The resulting mixture was transferred to a Ross Double Planetary Mixer. The sodium hydroxide was dissolved in the remaining water and this solution was slowly added to the mixture in the Ross, under constant agitation by the mix blades. When all of the sodium hydroxide solution had been added, a vacuum of 28"Hg was pulled and the resulting gel deaerated. The finished gel, which was transparent and had a pH of about 3.7, was packaged in light-resistant, laminated, flexible tubes.

A series of in vitro tests were performed to determine the tooth whitening ability of the inventive composition of Example 1. Bovine incisors, which had been imbedded in an acrylic matrix such that the buccal surfaces presented themselves on the top surface, were stained in a manner to duplicate the tooth staining observed in vivo by humans (alternately exposed to air and a staining broth at 37 degrees Celsius containing typticase soy broth, tea, coffee, mucin, $FeCl_3$, and Sarcina lutea, for a period of about four days). Each stained bovine incisor was numbered and measured for degree of initial staining (color by the CIELAB protocol) with a Minolta 5031 Spectrophotometer (3 mm aperture, 8 exposure averaging, outliers discarded). The CIELAB protocol evaluates color in terms of three axes of a color sphere, called L, a, and b. The "L" value is the axis in the color sphere which relates lightness and darkness on a scale from 0 (black) to 100 (white). The "a" value is the axis which relates color on a yellow to blue scale, with a 0 value in the center of the sphere, positive values toward the yellow, and negative values toward the blue. The "b" value is the axis which relates color on a red to green scale, with a 0 value in the center of the sphere, positive values toward the red, and negative values toward the green.

Once the bovine incisors have been stained, the bovine incisors were placed in contact with the CDP portion solution by daubing the surface of each incisor with an applicator until the surface of the tooth appeared moist. The moist incisor surface was then covered completely with the ACD portion gel, which was dispensed from the flexible tubes. All gels were kept in contact with the incisor surface for about 5 minutes, whereupon the tooth was rinsed clean of any gel residue with distilled water and swabbed with saliva (which had been previously collected and stored at 4 degrees Celsius).

The degree of stain removal was thereafter immediately determined by measuring the incisor surface for the final color, in the manner indicated above, and by comparing this final color with the initial color previously recorded for that incisor. The change in tooth color for each incisor is recorded in Table 1 below as ΔE. Absolute color change is defined as the square root of the sum of the squares of the changes of all color components (L, a, and b).

$$\sqrt{[(\Delta L)^2 + (\Delta a)^2 + (\Delta b)^2]} = \Delta E$$

Two bovine incisors were also treated with either just the CDP portion or the ACD portion.

The results for all treated incisors are recorded in Table 1 below.

TABLE 1

| Bovine Incisor # | Treatment | Initial Color | | | Final Color | | | ΔE |
|---|---|---|---|---|---|---|---|---|
| | | L | a | b | L | a | b | |
| 1 | CDP only | 45.38 | 3.68 | 10.42 | 47.11 | 3.21 | 10.09 | 1.82 |
| 2 | ACD only | 54.50 | −1.80 | 0.90 | 56.10 | −1.90 | 1.40 | 1.68 |
| 3 | CDP/ACD | 42.78 | 3.60 | 11.30 | 48.57 | 1.85 | 10.03 | 6.16 |
| 4 | CDP/ACD | 38.27 | 5.31 | 11.08 | 46.51 | 4.61 | 13.91 | 8.55 |
| 5 | CDP/ACD | 35.62 | 4.46 | 9.48 | 38.94 | 3.65 | 9.60 | 3.42 |
| 6 | CDP/ACD | 40.91 | 3.94 | 11.08 | 44.30 | 3.07 | 10.22 | 3.69 |
| 7 | CDP/ACD | 43.55 | 3.51 | 10.09 | 48.92 | 2.02 | 9.54 | 5.83 |

This table demonstrates that the inventive compositions, when applied as described above, are effective in removing tooth stains in an vitro stained bovine enamel model. The observed tooth whitening effect is much greater, when the CDP and ADP portions are both applied, than when either just the CDP Portion or the ACD Portion is applied.

What is claimed is:

1. A method for oxidizing tooth-staining chromogens to whiten teeth, the method comprising:
   (a) providing a first formulation having a chlorine dioxide precursor, the first formulation having a pH greater than approximately 7.0, and a second formulation having an acidulant capable of generating chlorine dioxide upon contact with the precursor, the second formulation being a gel having a gel pH of between approximately 3.0 and approximately 6.0;
   (b) applying the first formulation to a tooth in a subject's mouth;
   (c) putting the second formulation into a dental tray;
   (d) inserting the dental tray containing the second formulation into the subject's mouth, so as to generate a chlorine dioxide film at an interface between the precursor and the acidulant proximate the tooth; and
   (e) removing the dental tray after the tooth has been exposed to chlorine dioxide generated proximate to the tooth for a time period of between approximately five minutes and approximately sixty minutes.

2. A method according to claim 1, wherein the first formulation is a liquid, the liquid having a liquid pH.

3. A method according to claim 2, wherein the chlorine dioxide precursor is an alkali metal chlorite.

4. A method according to claim 3, wherein the chlorine dioxide precursor is sodium chlorite.

5. A method according to claim 4, wherein the liquid pH is between approximately 7.5 and approximately 9.0.

6. A method according to claim 5, wherein the liquid is aqueous.

7. A method according to claim 1, wherein the second formulation has an aqueous carrier and a polymeric, water soluble acidulant, the acidulant having a molecular weight greater than approximately 100,000.

8. A method according to claim 2, wherein the second formulation has an aqueous carrier and a polymeric, water soluble acidulant, the acidulant having a molecular weight greater than approximately 100,000.

9. A method according to claim 1, wherein the acidulant is selected from the group consisting of citric acid, carboxypolymethylene, and a combination thereof.

10. A method according to claim 2, wherein the acidulant is selected from the group consisting of citric acid, carhoxypolymethylene, and a combination thereof.

11. A method according to claim 4, wherein the second formulation has an aqueous carrier and a polymeric, water soluble acidulant, the acidulant having a molecular weight greater than approximately 100,000.

12. A method according to claim 11, wherein the acidulant is carboxypoly nethylene.

13. A method according to claim 12, wherein the carboxypolymethylene further acts as a thickener.

14. A method according to claim 12, wherein the gel pH is between approximately 3.0 and approximately 4.5.

15. A method for oxidizing tooth-staining chromogens to whiten teeth, the method comprising:
   (a) providing a first formulation having sodium chlorite as a chlorine dioxide precursor, the first formulation being a liquid having a liquid pH greater than 7.0, and a second formulation having carboxypolymethylene acting as an acidulant capable of generating chlorine dioxide upon contact with the precursor, the second formulation being a gel having a gel pH of between approximately 3.0 and approximately 6.0;
   (b) applying the first formulation to a tooth in a subject's mouth;
   (c) putting the second formulation into a dental tray;
   (d) inserting the dental tray containing the second formulation into the subject's mouth, so as to generate a chlorine dioxide film at an interface between the precursor and the acidulant proximate the tooth, wherein proximate to the film, a film pH is between approximately 3.0 and approximately 6.0; and
   (e) removing the dental tray after the tooth has been exposed to chlorine dioxide generated proximate to the tooth for a time period of between approximately five minutes and approximately sixty minutes.

16. A method according to claim 15, wherein the carboxypolymethylene further acts as a thickener.

17. A method according to claim 16, wherein the liquid is aqueous.

18. A method according to claim 17, wherein the gel pH is between approximately 3.0 and approximately 4.5.

* * * * *

UNITED STATES PATENT AND TRADEMARK OFFICE
CERTIFICATE OF CORRECTION

PATENT NO. : 5,944,528
DATED : August 31, 1999
INVENTOR(S) : R. Eric Montgomery

It is certified that error appears in the above-identified patent and that said Letters Patent is hereby corrected as shown below:

Column 8, line 18, change the words "carboxypoly nethylene" to one word "carboxypolymethylene"

Signed and Sealed this

Thirty-first Day of October, 2000

Attest:

Q. TODD DICKINSON

Attesting Officer

Director of Patents and Trademarks